(12) United States Patent
Zhang et al.

(10) Patent No.: US 9,976,950 B2
(45) Date of Patent: May 22, 2018

(54) OPTICAL DETECTOR MODULE, MEASUREMENT SYSTEM AND METHOD OF DETECTING PRESENCE OF A SUBSTANCE IN A TEST MATERIAL

(71) Applicant: ASTON UNIVERSITY, Birmingham, West Midlands (GB)

(72) Inventors: Lin Zhang, Birmingham (GB); Zhijun Yan, Birmingham (GB); Kaiming Zhou, Birmingham (GB); Mehmet Aytun Erdentug, Broadway (GB)

(73) Assignee: ASTON UNIVERSITY, Birmingham, West Midlands (GB)

( * ) Notice: Subject to any disclaimer, the term of this patent is extended or adjusted under 35 U.S.C. 154(b) by 0 days. days.

(21) Appl. No.: 15/517,706

(22) PCT Filed: Oct. 7, 2015

(86) PCT No.: PCT/EP2015/073163
§ 371 (c)(1),
(2) Date: Apr. 7, 2017

(87) PCT Pub. No.: WO2016/055527
PCT Pub. Date: Apr. 14, 2016

(65) Prior Publication Data
US 2017/0307522 A1   Oct. 26, 2017

(30) Foreign Application Priority Data
Oct. 9, 2014   (GB) .................................. 1417887.5

(51) Int. Cl.
*G01N 21/00*     (2006.01)
*G01N 21/47*     (2006.01)
(Continued)

(52) U.S. Cl.
CPC ........... *G01N 21/47* (2013.01); *G01N 21/359* (2013.01); *G02B 6/02085* (2013.01); *G01N 33/02* (2013.01); *G01N 2021/4719* (2013.01)

(58) Field of Classification Search
CPC ... G01J 3/02; G01J 3/51; G01N 21/65; G01N 15/1459; G01N 21/47; G01N 21/359; G02B 6/02085
See application file for complete search history.

(56) References Cited

U.S. PATENT DOCUMENTS 5,848,204 A * 12/1998 Wanser .................. G01L 1/246
385/12
2014/0203389 A1   7/2014 Neukom et al.

FOREIGN PATENT DOCUMENTS

| EP | 1 085 315 A1   | 3/2001 |
| GB | 2372096 A      | 8/2002 |
| WO | 2003/040704 A1 | 5/2003 |

OTHER PUBLICATIONS

British Search Report dated Mar. 19, 2015 issued in Great Britain Patent Application No. 1417887.5.
(Continued)

*Primary Examiner* — Abdullahi Nur
(74) *Attorney, Agent, or Firm* — Troutman Sanders LLP

(57) ABSTRACT

Embodiments of the invention comprise apparatus and methods for detecting the presence of a substance in a test material using a plurality of wavelength-specific couplers (e.g. tilted fiber gratings) which provide a spatially distributed multi-node all-optical measurement system. Each node of the measurement system can comprise an optical module that is sensitive to the intensity of a limited band of wavelengths. The node is thus capable of detecting the presence of an absorption peak in a spectrum without having to obtain the full spectrum. By providing a plurality of optical modules that are sensitive to different wavelengths, the spectral
(Continued)

signature of different substances may be monitored without having to measure full spectra. The measurement system may be particularly useful in a process control environment where it is desirable to take measurements of one or more substances in different locations.

20 Claims, 1 Drawing Sheet

(51) Int. Cl.
G01N 21/359 (2014.01)
G02B 6/02 (2006.01)
G01N 33/02 (2006.01)

(56) References Cited

OTHER PUBLICATIONS

International Search Report and PCT Written Opinion dated Apr. 22, 2016 issued in corresponding PCT International Application No. PCT/EP2015/073163.

* cited by examiner

OPTICAL DETECTOR MODULE, MEASUREMENT SYSTEM AND METHOD OF DETECTING PRESENCE OF A SUBSTANCE IN A TEST MATERIAL

CROSS-REFERENCE TO RELATED APPLICATIONS

This application is the U.S. National Phase of International Patent Application No. PCT/EP2015/073163, filed Oct. 7, 2015, which claims priority to United Kingdom Patent Application No. 1417887.5, filed Oct. 9, 2014, the contents of each of which are incorporated herein by reference in their entirety.

TECHNICAL FIELD

The invention relates to a spectroscopic optical sensor, e.g. for use in a process control system in a materials manufacturing apparatus. In particular, the invention relates to a near-infrared (NIR) spectroscopic detector for use in detecting a plurality of different properties of a test material, which may be a foodstuff (e.g. flour), a polymer, or the like.

BACKGROUND TO THE INVENTION

NIR spectroscopy is used in the process control methods within the food industry because the spectra associated with a foodstuff may provide information about the chemical bonds contained within a foodstuff under test. With suitable calibration, a detected spectrum for a test foodstuff can be used to determine the concentration of various components of the test foodstuff, such as water (e.g. moisture), protein, fat and carbohydrate. Herein, the term "foodstuff" may mean a material used at any stage during the production of a food product, i.e. any ingredient, intermediate substance or even the final product itself.

Conventional NIR spectroscopy techniques use a diode array detector to detect the spectrum of a foodstuff, which is subsequently analysed to obtain information about the constituents of the foodstuff.

SUMMARY OF THE INVENTION

At its most general, the present invention proposes an optical sensor having a plurality of wavelength-specific couplers (e.g. tilted fibre gratings) which provide a spatially distributed multi-node all-optical measurement system. Each node of the measurement system may comprise an optical module that is sensitive to (i.e. capable of detecting variations in) the intensity of a limited band of wavelength (preferably a single wavelength). The node is thus capable of detecting the presence of an absorption peak in a spectrum without having to obtain the full spectrum. By providing a plurality of optical modules that are sensitive to different wavelengths, the spectral signature of different substances may be monitored without having to measure full spectra.

The modularity of the system enables easy control over both the location and function of each node. The measurement system may be particularly useful in a process control environment where it is desirable to take measurements of one or more substances in different locations. An optical module adapted to detect an absorption peak associated with a particular substance can be mounted in each location where detection is required. Analysis of the signal detected at each node may be performed centrally.

According to the invention, there may be provided a measurement system for detecting the presence of a substance in a test material, the measurement system comprising: a source of optical radiation; an optical waveguide coupled to the source to carry the optical radiation; a plurality of optical detection nodes at spatially separated locations along the optical waveguide, wherein each of the plurality of optical detection nodes comprises: an optical coupler arranged to couple substance-specific optical radiation out of the optical waveguide into test material, and an optical detector arranged to measure the intensity of the substance-specific optical radiation that is scattered by the test material; and a processor arranged to determine the presence of a substance in the test material at each of the plurality of detection nodes based on the measured intensity obtained at the respective optical detector in each of the plurality of optical detection nodes. The system may thus provide an all optical detection mechanism in which a plurality of spatially separated measurement nodes are served by a common light source, and preferably a common optical waveguide.

Herein, the term "substance-specific optical radiation" may mean optical radiation having a predetermined wavelength at which it is known that the presence of a certain substance exhibits a detectable spectral response. It may be a narrow band of wavelengths or even a single wavelength. The substance-specific optical radiation may a limited subset of wavelengths carried by the optical waveguide. For example, the source may a broadband, e.g. white light, source such as a filament bulb. The substance-specific optical radiation may be a narrow band of wavelengths, e.g. having a bandwidth of 20 nm or less. In practice, the bandwidth of the substance-specific optical radiation may be chosen depending on the material to be detected, because absorption lines can be broad or narrow depending on the substance. For example, water absorption peaks can be very broad (up to several hundred nm) whereas some gas absorptions can be very narrow.

Herein, the term "optical radiation" is used in the conventional sense to mean electromagnetic radiation in the ultraviolet (UV), visible and infrared parts of the spectrum, i.e. radiation having a wavelength in the range 100 nm to 1 mm. The invention may be particularly useful in the near infrared (NIR) part of the spectrum, e.g. having wavelengths from 780 nm to 3 µm, since it is known that the absorption spectra of certain substances of interest, e.g. water, protein, fat, etc. exhibit signature peaks in this range, as is well known. But in principle the invention may be used at any optical wavelength where as response is observable.

The optical waveguide may comprise guiding material that extends along the optical axis and is surrounded by cladding material. The optical coupler may be fabricated directly into the optical waveguide, e.g. as a grating section comprising a plurality of modulations of the guiding material's refractive index, wherein each refractive index modulation lies on a plane that has a normal at an oblique angle relative to the optical axis. The waveguide may be an optical fibre, wherein the grating section is formed in a core of the fibre (which corresponds to the guiding material mentioned above). The optical coupler may thus be a tilted fibre grating (also known as tilted fibre Bragg gratings).

The tilted fibre grating may have a uniform grating period for coupling a single primary wavelength, which forms the substance-specific radiation. The tilted fibre grating may comprise a plurality of refractive index modulation in the optical fibre, wherein each refractive index modulation lies on a plane that has a normal at 45° relative to the optical axis. Tilted fibre gratings may be fabricated by any suitable inscription technique, e.g. UV-inscription. UV-inscription is a relatively simple and direct "printing" process, which does not require removal of the fibre cladding or non-circular core fibres. This make enable detection nodes to be fabricated into an optical waveguide after it is laid in a processing environment.

Each of the plurality of detection nodes may include a scattered signal collector disposed between the test material and optical detector to collect the substance-specific optical radiation scattered by the test material. Such a collector is useful if the scattered signal is weak. It may improve detection efficiency and reduce the impact of noise. The scattered signal collector may be an integrating sphere or large active area detector.

It may be desirable for the measurement system to detect different substances. To achieve this, a plurality of different types of substance-specific optical radiation may be coupled out of the optical waveguide at the plurality of optical detection nodes. Put another way, whilst each detection node may be set up to detect a particular wavelength, the plurality of optical detection nodes need not all detect the same wavelength. Thus, the plurality of optical detection nodes may comprise: a first optical detection node whose optical coupler is arranged to couple substance-specific optical radiation having a first wavelength, and a second optical detection node whose optical coupler is arranged to couple substance-specific optical radiation having a second wavelength, wherein the first wavelength is different from the second wavelength. The system may be configured to detect two, three, four, five or more different substances, and therefore may comprise an optical detection node with a different substance-specific optical radiation configuration for each respective substance.

The processor may be a central controller provided on a conventional computer. However, in one embodiment the processor may be distributed among the optical detection nodes, i.e. the processor may comprise a plurality of sub-processors, each of which is located in a respective optical detection node.

The processor may have access to a computer memory that stores a calibration look-up table which was prepopulated in a preliminary calibration procedure to map detected intensities on to quantitative scores representing the concentration of the substance in the test material. The processor may thus be arranged to output a quantitative indication of amount of the substance present in the test material by comparing the measured intensity with the look-up table.

Alternatively or additionally, a baseline comparison may be made in real time for each measurement. In this arrangement, each of the plurality of optical detection nodes may comprises a reference coupler arranged to couple a reference signal out of the optical waveguide before the substance-specific optical radiation is coupled out by the optical coupler. The processor may be arranged to determine the presence of a substance in the test material at each of the plurality of detection nodes based on both the reference signal and the measured intensity obtained at that respective optical detection node. Providing the reference signal prevents variations in the intensity of the source of optical radiation from affecting the measurements.

The reference signal at each of the plurality of optical detection nodes may consist of the same substance-specific optical radiation as is coupled out of the optical waveguide by the optical coupler at that respective optical detection node. The reference coupler in each optical detection node may also be a tilted fibre grating fabricated directly in the optical waveguide. The coupling strength of this tilted fibre grating may be less than the coupling strength of the tilted fibre grating that acts as the optical coupler.

In another aspect, the present invention may provide a discrete detector module for use with the measurement system outlined above. Thus, there may be provided an optical detector module for detecting the presence of a substance in a test material, the module comprising: a housing having a optically transparent test window formed therein; a optical fibre disposed in the housing, the optical fibre having a tilted fibre grating fabricated therein, the tilted fibre grating being arranged to couple substance-specific optical radiation out of the optical fibre through the test window into test material; an optical detector disposed in the housing and arranged to measure the intensity of the substance-specific optical radiation that is scattered by the test material back through the test window; and a signal collector (e.g. integrating sphere) disposed between the test window and optical detector to collect the substance-specific optical radiation scattered by the test material.

In a further aspect, the invention may provide a method of detecting the presence of a substance in a test material, the method comprising: introducing optical radiation into an optical waveguide; coupling substance-specific optical radiation out of the optical waveguide into test material at a plurality of spatially separated locations along the optical waveguide; measuring an intensity of the substance-specific optical radiation that is scattered by the test material at each of the plurality of spatially separated locations along the optical waveguide; and determining a presence of a substance in the test material at each of the plurality of detection nodes based on the measured intensity obtained at each of the plurality of spatially separated locations along the optical waveguide.

The method may be carried out using any one or more features of the system outlined above. In particular, the step of measuring the intensity of the scattered substance-specific optical radiation may comprise: collecting, e.g. using an integrating sphere or a large active area detector, the substance-specific optical radiation scattered by the test material at each of the plurality of spatially separated locations along the optical waveguide, and inputting the collected substance-specific optical radiation to an optical detector to measure its intensity. In a preferred embodiment, the step of coupling substance-specific optical radiation out of the optical waveguide into test material may comprise providing a tilted fibre grating in the optical waveguide, wherein the grating period of the tilted fibre grating is selected to couple a predetermined wavelength of optical radiation out of the optical waveguide.

BRIEF DESCRIPTION OF THE DRAWINGS

An embodiment of the invention is discussed below with reference to the accompanying drawings, in which.

DETAILED DESCRIPTION; FURTHER OPTIONS AND PREFERENCES

Figure 1:
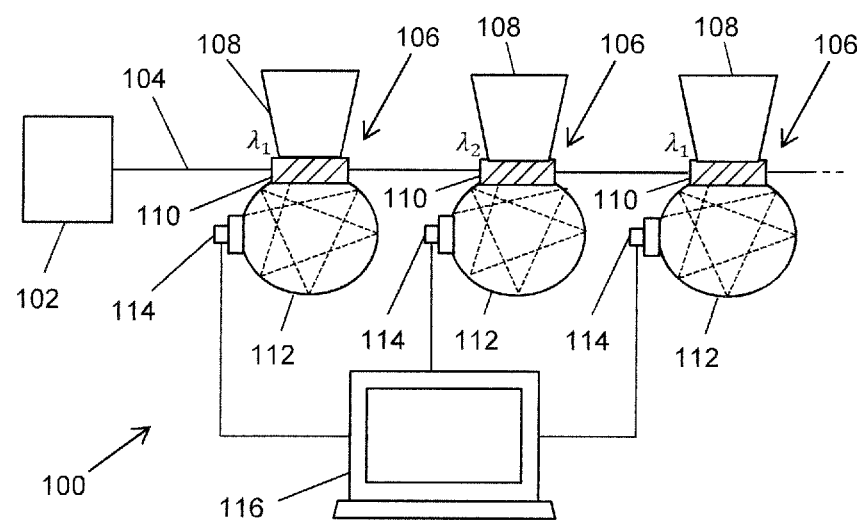
FIG. 1 is a multi-node optical measurement system that is a first embodiment of the invention.

FIG. 1 shows a multi-node optical measurement system 100 that is an embodiment of the invention. The system 100 comprises a light source 102, e.g. a white light source such as a halogen bulb, arranged to output radiation in the near-infrared (NIR) wavelength range, e.g. from 900 nm to 1900 nm. The output radiation is coupled into an optical waveguide 104, e.g. an optical fibre, in a conventional manner. The optical fibre may be a conventional silica-based fibre having a core for conveying the radiation surrounded by a cladding layer.

The optical waveguide 104 extends through a processing environment (not shown) in which it is desirable to detect one or more properties of material being handled in that environment (referred to herein as a "test material"). For example, the processing environment may be for manufacturing flour, where it is desirable regularly to detect the quality of the flour, e.g. by detecting its moisture content, protein content or fat content. The measurement system of the invention may be applicable in other types of processing environment, e.g. milk powder preparation, powdered pharmaceutical preparation, polymer processing, bread making, etc. In principle the measurement system of the invention may be applied to any processing method which involves a test material (which may be gas, liquid or powder) that will scatter incident radiation from the light source.

In order to detect properties of a test material in the processing environment, the measurement system of the invention provides a plurality of detection nodes 106 along the optical waveguide 104. Three detection nodes 106 are shown in FIG. 1, but the invention is not limited to this number of nodes. The measurement system may provide as many nodes on the optical waveguide 104 as can be supported by the optical power generated by the light source 102.

Each detection node 106 includes test window 108 arranged to receive or hold therein a sample of the test material. The test window 108 may be a receptacle for receiving an extracted sample of the test material. However, in a preferred embodiment, the test window is simply an optically transparent cover that provides a protective barrier between the test material in situ in the processing environment and the components of the node. Each detection mode may thus be mounted within a protective transparent casing provided by the test window 108 in a suitable location (e.g. conveyor belt, mixing chamber, etc.) in the processing environment.

Each detection node 106 includes an optical coupler 110 for coupling light conveyed by the optical waveguide 104 into the test window 108 to interact with (i.e. scatter from) the test material. In this embodiment, each optical coupler 110 is a tilted fibre grating. Each tilted fibre grating may be fabricated integrally with the optical waveguide 104, which reduces the total number of components in the system and may reduce losses that occur at the transitions between different components.

Herein a tilted fibre grating means a section of optical waveguide having a guiding material (e.g. the core of an optical fibre) surrounding by cladding material, wherein the guiding material includes a plurality of regularly (preferably periodically) spaced refractive index modulations along an optical axis of the guiding material, and wherein each refractive index modulation lies on a plane that has a normal at an oblique angle relative to the optical axis. The refractive index modulation may be fabricated in a known manner, e.g. using UV inscription techniques.

Each detection node 106 may have an optical coupler 110 arranged to couple out of the optical waveguide a limited sub-range of wavelengths from the optical radiation from the light source 102. In the embodiment shown in FIG. 1, each optical coupler 110 is arranged to couple out optical radiation at a single wavelength. For example, in FIG. 1 the first and third optical couplers 110 couple out wavelength $\lambda_1$, whereas the second optical coupler 110 couples out wavelength $\lambda_2$. The wavelength or wavelengths that are coupled from a tilted fibre grating depends on the period of the grating, i.e. the separation of the refractive index modulations. The coupled wavelengths may thus be selected in advance, e.g. to correspond to a wavelength at which it is known that the presence of a certain substance (e.g. water or protein) exhibits a detectable spectral response. In other words, the coupled optical radiation may be specific to the substance which is desired to be detected, i.e. "substance-specific optical radiation".

The magnitude of the signal that is coupled out of the optical waveguide 104 by each tilted fibre grating is related to the coupling strength of the tilted fibre grating. The coupling strength is in turn related to both the amount (e.g. duration) of UV exposure during fabrication of the refractive index modulations and also the size of the oblique angle between the normal of the plane of the refractive index modulation and the optical axis. In a preferred embodiment the oblique angle is 45°, which is optimal for coupling light out of the optical waveguide. The overall coupling strength may be selected to ensure that enough light is coupled into the test material to provide a useful response, whilst ensuring that enough optical power remains for the remaining detection nodes.

Each detection node 106 also includes a scattered signal collector 112. The scattered signal collector 112 is arranged to collect optical radiation coupled out of the optical waveguide that is subsequently scattered by the test material. In the embodiment shown in FIG. 1, each scattered signal collector 112 is a integrating sphere which effectively converts the scattered radiation from the test material into a uniform output received by an optical detector 114. The integrating sphere is particularly useful because of its high detection efficiency (relatively little optical power is lost in transferring the scattered signal to the optical detector 114) and because of its low noise profile. However, the scattered signal collector may be implemented in other ways, e.g. by using an large active area detector or the like.

Each optical detector 114 may be a photo detector (e.g. CCD or the like) arranged to detect an intensity of incident light from the scattered signal collector 112. An output from each optical detector 114 is transmitted to a control computer 116 for subsequent analysis and/or interpretation.

In one embodiment, each node of the measurement system 100 may assess relative changes in the intensity of light detected by the optical detector 114 in order to determine the presence of a substance in the test material. For example, where the coupler 110 is arranged to couple a wavelength $\lambda_1$ that is known to have a specific response to water, a detected decrease in intensity of the scattered signal for this wavelength will be indicative of an increase in the amount of water present in the test material.

Herein, the term "specific response" means that the wavelength concerned in known to be absorbed or otherwise coupled to the substance in question, but does not elicit a similar response from other types of test material. Traditional, different test materials were distinguished by compared there entire spectral response over a range of wavelengths. The present invention proposes to select a particular wavelength (or possibly a narrow band of wavelengths) which exhibit specificity for a given substance. In principle there is then no limit to the number of substances that can be detected by the system; all that is needed is an optical coupler that can couple the relevant wavelength into the test material. The invention thus enables both multi-location and multi-substance detection using a common optical source.

Moreover, through suitable calibration, the system shown in FIG. 1 may be able to provide quantitative information about the concentration of the detected substance in the test material. For example, the control computer 116 may have a calibration look-up table stored thereon, which is arranged to map a detected intensity at each detection node 106 to a concentration value for the substance to be detected.

However, a predetermined calibration look-up table may not be able to take account of variations in light intensity of the source nor of any changes in the optical waveguide setup that may occur between calibration and normal operation. To address this issue, a reference signal (or base line signal) may be obtained for each detection node 106, wherein the reference signal provides a indication of the optical radiation input to the optical coupler 110. The reference signal is preferably limited to the same wavelength or small band of wavelengths that are coupled out of the optical waveguide 104 by the optical coupler 110. The optical signal detected at the detector 114 may thus be compared with the reference signal to determine accurately intensity changes caused by scattering and absorption in the test material.

Figure 2:
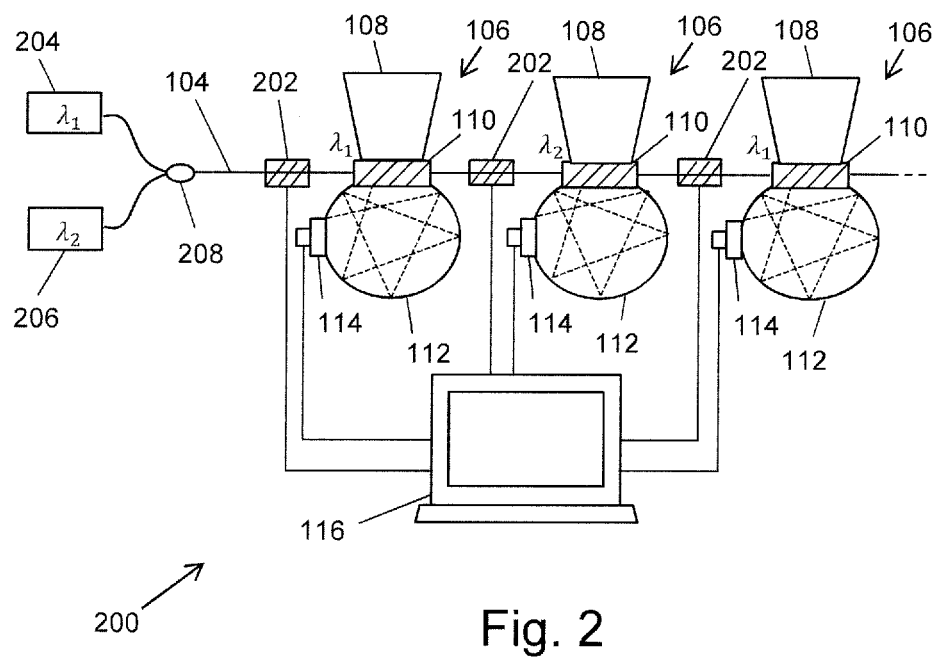
FIG. 2 is a multi-node optical measurement system that is a second embodiment of the invention.

FIG. 2 shows a multi-node optical measurement system 200 that is an embodiment of the invention and which includes components for providing the reference signal mentioned above. Features in FIG. 2 which perform the same functions as in FIG. 1 are given the same reference numbers and are not described again.

In FIG. 2, a respective reference coupler 202 is provided on the optical waveguide 104 in advance of each detection node 106. In this embodiment, each reference coupler 202 is a tilted fibre grating integrally formed in the optical waveguide, e.g. in a manner similar to the optical coupler 110 discussed above. However, in order to ensure that the reference coupler 202 does not couple too much optical power out of the optical waveguide 104, the tilted fibre grating that acts as the reference coupler 202 is fabricated to have a much lower coupling strength than the tilted fibre grating that acts as the optical coupler 110. For example, the coupling strength of the reference coupler 202 may be one tenth (0.1) of the coupling strength of the optical coupler 110. In order to couple the same wavelength (of band of wavelengths) as the optical coupler 110 in its respective detection node 106, the tilted fibre grating that acts as the reference coupler 202 may have the same spatial configuration of refractive index modulations (e.g. the same oblique angle and grating period) as the tilted fibre grating that acts as the optical coupler. However, the grating length and/or UV exposure duration may be reduced for the tilted fibre grating that acts as the reference coupler 202, in order to provide a lower coupling strength.

A reference signal coupled out of the optical waveguide 104 by each reference coupler 202 is input to the central computer 116, where it is compared with the output from the optical detector 114 in the respective detection node 106.

FIG. 2 also differs from FIG. 1 in that the light source comprises a first laser diode 204 that emits coherent optical radiation at a first wavelength $\lambda_1$ and a second laser diode 206 that emits coherent optical radiation at a second wavelength $\lambda_2$. The optical radiation emitted by the first laser diode 204 and second laser diode 206 are coupled into the optical waveguide 104 by a coupler 208 that operates in a conventional manner. The measurement system of the invention may thus operate with either a broadband source or with one or more discrete wavelength sources. This means that the wavelength selectivity of the detection nodes may be provided through either or a combination of selectivity at the light source and selectivity provided by the width of the spectral response of the tilted fibre grating.

In FIGS. 1 and 2, each detection node 106 is shown as being in communication with a central control computer 116. In practice, however, it may be desirable for each detection node 106 to include a local processor for receiving the signals from the optical detector 114 (and the reference coupler 202, if present). This may minimise the optical path travelled by the signals after detection, which can reduce errors caused by post-measurement disturbances. Each detection node 106 may further include means to wirelessly communicate the results of their measurements to a remote control computer. This arrangement may facilitate installation of the system, since the optical waveguide 104 is the only necessary physical connection between each detection node and the optical source 102.

Each detection node 106 may be provided as a separate module, e.g. encased in a housing that protects (e.g. encloses) the components and which includes a test window that is transmissive to the coupled and scattered optical radiation.

FIGS. 1 and 2 show a plurality of detection nodes 106 in series along a single optical waveguide 104 that extends from an optical source 102. However, in other embodiments, a plurality of optical waveguides 104 may extend from the optical source 102, each optical waveguide having one of more detection nodes 106 provided thereon. The detection nodes may thus be connected in series and/or parallel with each other.

The measurement system of the invention may be incorporated into a process control system in a manufacturing environment. The results of the measurement system, i.e. the detection (qualitative or quantitative) of a substance in the test material, may be used to adjust control parameters for manufacture, e.g. for subsequent processing steps concerning the test material ("feed-forward" control) or for future operation of past processing steps ("feed-back" control).

The invention claimed is:

1. A measurement system for detecting the presence of a substance in a test material, the measurement system comprising:
    a source of optical radiation;
    an optical waveguide coupled to the source to carry the optical radiation;
    a plurality of optical detection nodes at spatially separated locations along the optical waveguide, wherein each of the plurality of optical detection nodes comprises:
        an optical coupler arranged to couple substance-specific optical radiation out of the optical waveguide into test material, and
        an optical detector arranged to measure the intensity of the substance-specific optical radiation that is scattered by the test material; and
    a processor arranged to determine the presence of a substance in the test material at each of the plurality of detection nodes based on the measured intensity obtained at the respective optical detector in each of the plurality of optical detection nodes.

2. The measurement system according to claim 1, wherein the substance-specific optical radiation comprises optical radiation having a predetermined wavelength at which it is known that the presence of a certain substance exhibits a detectable spectral response.

3. The measurement system according to claim 1, wherein the optical coupler is fabricated directly into the optical waveguide.

4. The measurement system according to claim 1, wherein the optical waveguide is an optical fibre and the optical coupler is a tilted fibre grating.

5. The measurement system according to claim 4, wherein the tilted fibre grating as a uniform grating period for coupling a single primary wavelength.

6. The measurement system according to claim 4, wherein the tilted fibre grating comprising a plurality of refractive index modulation in the optical fibre, wherein each refractive index modulation lies on a plane that has a normal at an oblique angle relative to the optical axis.

7. The measurement system according to claim 6, wherein the oblique angle is 45°.

8. The measurement system according to claim 1, wherein each of the plurality of detection nodes includes a scattered signal collector disposed between the test material and optical detector to collect the substance-specific optical radiation scattered by the test material.

9. The measurement system according to claim 8, wherein the scattered signal collector is an integrating sphere.

10. The measurement system according to claim 1, wherein the plurality of optical detection nodes comprises:
a first optical detection node whose optical coupler is arranged to couple substance-specific optical radiation having a first wavelength, and
a second optical detection node whose optical coupler is arranged to couple substance-specific optical radiation having a second wavelength,
wherein the first wavelength is different from the second wavelength.

11. The measurement system according to claim 1, wherein the source is a broadband source of optical radiation.

12. The measurement system according to claim 1, wherein the processor comprises a plurality of distributed sub-processors, each of the plurality of distributed sub-processors being located in a respective optical detection node.

13. The measurement system according to claim 1, comprising a computer memory accessible by the processor, wherein the computer memory has a calibration look-up table stored thereon and wherein the processor is arranged to output a quantitative indication of amount of the substance present in the test material by comparing the measured intensity with the look-up table.

14. The measurement system according to claim 1, wherein each of the plurality of optical detection nodes comprises a reference coupler arranged to couple a reference signal out of the optical waveguide before the substance-specific optical radiation is coupled out by the optical coupler, and wherein the processor is arranged to determine the presence of a substance in the test material at each of the plurality of detection nodes based on both the reference signal and the measured intensity obtained at that respective optical detection node.

15. The measurement system according to claim 14, wherein the reference signal at each of the plurality of optical detection nodes consists of the same substance-specific optical radiation as is coupled out of the optical waveguide by the optical coupler at that respective optical detection node.

16. The measurement system according to claim 14, wherein:
the optical waveguide is an optical fibre,
the optical coupler in each optical detection node is a first tilted fibre grating fabricated directly in the optical fibre,
the reference coupler in each optical detection node is a second tilted fibre grating fabricated directly in the optical fibre,
the grating period of the second tilted fibre grating is the same as the grating period of the first tilted fibre grating, and
the coupling strength of the second tilted fibre grating is less than the coupling strength of the first tilted fibre grating.

17. An optical detector module for detecting the presence of a substance in a test material, the module comprising:
a housing having a test window formed therein;
a optical fibre disposed in the housing, the optical fibre having a tilted fibre grating fabricated therein, the tilted fibre grating being arranged to couple substance-specific optical radiation out of the optical fibre through the test window into test material;
an optical detector disposed in the housing and arranged to measure the intensity of the substance-specific optical radiation that is scattered by the test material back through the test window; and
a signal collector disposed between the test window and optical detector to collect the substance-specific optical radiation scattered by the test material.

18. The method of detecting the presence of a substance in a test material, the method comprising:
introducing optical radiation into an optical waveguide;
coupling substance-specific optical radiation out of the optical waveguide into test material at a plurality of spatially separated locations along the optical waveguide;
measuring an intensity of the substance-specific optical radiation that is scattered by the test material at each of the plurality of spatially separated locations along the optical waveguide; and
determining a presence of a substance in the test material at each of the plurality of detection nodes based on the measured intensity obtained at each of the plurality of spatially separated locations along the optical waveguide.

19. The method according to claim 18, wherein the step of measuring the intensity of the scattered substance-specific optical radiation comprises:
collecting the substance-specific optical radiation scattered by the test material at each of the plurality of spatially separated locations along the optical waveguide, and
inputting the collected substance-specific optical radiation to an optical detector to measure its intensity.

20. The method according to claim 18, wherein the step of coupling substance-specific optical radiation out of the optical waveguide into test material comprises providing a tilted fibre grating in the optical waveguide, wherein the grating period of the tilted fibre grating is selected to couple a predetermined wavelength of optical radiation out of the optical waveguide.

* * * * *